United States Patent [19]

Michnick et al.

[11] Patent Number: 5,037,301

[45] Date of Patent: Aug. 6, 1991

[54] METHOD ENABLING DENTAL IDENTIFICATION OF HUMANS AND ANIMALS

[75] Inventors: Bruce T. Michnick, Plainview; Stanley Kitzis, Woodbury, both of N.Y.

[73] Assignee: Dentistry Researchers & Designers Inc., Huntington, N.Y.

[21] Appl. No.: 437,807

[22] Filed: Nov. 17, 1989

[51] Int. Cl.$^5$ ................................................ A61C 5/00
[52] U.S. Cl. ...................................... 433/229; 433/215
[58] Field of Search ................................. 433/229, 215

[56] References Cited

U.S. PATENT DOCUMENTS 2,995,633  8/1961  Puharich et al. ................. 433/229
4,512,744  4/1985  Michnick et al. ................. 433/229

Primary Examiner—John J. Wilson
Assistant Examiner—Cindy A. Cherichetti
Attorney, Agent, or Firm—Charles I. Bradsky

[57] ABSTRACT

Message identifying information in available microdot and microchip format is applied to a tooth, where it can be easily coated over, yet still readable by appropriate scanning devices. The microdot or microchip can be a passive device, for external reading, or can be active to transmit information to the scanner.

8 Claims, No Drawings

METHOD ENABLING DENTAL IDENTIFICATION OF HUMANS AND ANIMALS

FIELD OF THE INVENTION

This invention relates to the science of identification, in general, and to a method for the dental identification of humans and animals, in particular.

BACKGROUND OF THE INVENTION

As is well known and understood, several methods are employed in identifying the remains of those killed in accidents, disasters, and/or natural and man-made cataclysmic holocausts. If photographs are not helpful, resort is often made to the use of fingerprints as a means of identification—but the problem with that is that those whose fingerprints are on file represents only an infinitesimal number of persons, and the fingerprinting of school-age children is just beginning, although continuing to be met with resistance. Dental records are employed, but only after some idea exists as to the identity of the person sought to be substantiated, and, really, of limited usefulness. While the use of "dog-tags" in the military continues to be a common practice, instances often arise where the "dog-tags" are destroyed, missing, or otherwise not available for purposes of identification.

And, no matter what the above restrictions offer as regards the identification of humans, the identification of animals is a far greater problem. Besides the issuance of license tags—except for photographs of the animals in question, or the availability of other visual indicia—, the only technique usually available involves a process of "branding", limited to race-horses and cattle, in general.

Additionally, more and more in todays world, a problem exists concerning "missing" children whose parents cooperate with Governmental Agencies in an attempt to locate them throughout the country and world by means of various advertising. Photographic means of identification are quite limited in this respect as time goes by, as the features of the child undergo significant changes with time. Although the search for the missing child continues, the chances of success significantly decrease with the passage of the years, and it is only in the rare circumstance that an accidental identification is later made. Such limitation of the use of photographic evidence is also apparent in the detection of terrorists at airport, railroad and bus locations, because of the ease with which one may change his or her appearance to meet the appropriate circumstances. This same limitation exists with respect to "most-wanted" people in general, and their identification usually does not follow until after the fact, i.e., when the person has committed an act sought to be prevented, after apprehension, or through the identification of remains.

DETAILED DESCRIPTION OF THE INVENTION

In accordance with the method of the invention, microdot and microchip technology is combined with readily available and understood dental techniques in applying message identifying information characteristics to a tooth in simple, inexpensive manner. In accordance with present day techniques, the microdot can have enscribed upon it any and all information pertinent to the human or animal—such as Social Security numbers, name, address and telephone information, fingerprint designations, health information, serial numbers for animals, and any other indicia of identification desired, and such information can easily be encoded into a microchip. Such information can be inscribed on a microdot in any available technology—such as with alphanumerics, strip, disc or bar-line codes—and can be inscribed on either a plastic, paper, or metal disc of an approximate four millimeter size; on a microchip, such information can similarly be encoded, along with such items as country of origin, passport numbers, names and addresses of persons to be contacted, coded identification pertaining only to the individual, from which access to a data base can be had to provide any of the information outlined above, or otherwise. In a preferred embodiment of the present invention, such encoded disc or chip is embedded in prescribed manner on the tooth of the human, or animal, with a lower right molar in humans being particularly attractive. Such attractiveness results from the ease in which visual scanners, and/or laser beam techniques can be utilized in "reading" the information on the tooth face, in any appropriate manner, but the embedding can be carried out on any tooth, or in a denture, or in any other place available to a dentist when working with the patient. (In this regard, it should be appreciated that almost every school-age child is required to visit the dentist before classes begin, every member of the armed services undergoes a dental examination as part of the induction process, and the same is true with respect to newly admitted inmates at a prison facility. There, it is but a simple task to insert the microdot, or microchip into position, at which point it will forever remain and provide its output information during later interrogation. Thereafter, information can be provided to the armed services, police authorities, dentists and school officials, for example, who possess these interrogating scanners as to identification of those individuals who are "missing", or who should be otherwise looked after, and the output information detected by any of the commercially available scanners used will remain the same even though physical features of the individual may change with time, or be intentionally altered.)

In carrying out the method of the invention, a self-limiting dental drill is utilized, corresponding to the size of the microdot, microdisc, or microchip. With such drill, the tooth face, the tooth itself, or the denture, can be prepared to a predetermined depth of an amount requiring no anesthesia. Although a dental drill is especially easy for preparing an initial cavity for the insertion of the information medium, other preparation techniques may be employed—e.g. the use of laser beams, ultrasonic drilling, etc.

Once the drilling or other means has been utilized to provide the depth required, a standard "acid-etching technique" can be utilized, in which an acid (typically 35% to 50% stabilized phosphoric acid) is applied to the area in question for approximately 60 seconds. After washing with water and drying, the dot, disc or chip medium can be placed in the prepared area under contamination free conditions. Once the dot, disc or chip medium is allowed to dry, a layer of clear, composite material can be applied to cover the information medium and to fill the cavity established. Such a composite resin thus embeds the dot, disc, or chip in the tooth, or on its face, or in a denture, to become a permanent identification record. One such composite resin which can be employed is marketed under the the brand name "COMPLUS", by the Parkel Company of Farmingdale, N.Y. Such composite, however, can be any appropriate white light cured material, or a catalyst, e.g. BIS GNA, induced composite.

When so prepared, the tooth—be it of a human or of an animal—, is marked for life. If an occasion thereafter arises by which some means of identification is required, an available scanning technique, even using hand-held apparatus, can be employed. Depending upon the information imparted to the microdot, microdisc, microchip or other informational medium, an investigator can identify the individual, and can be provided with other emergency information, as medical status, allergy information, persons to contact in cases of emergency, etc., as well as all the identification information alluded to above. Alternatively to providing an entire readout, it will be readily apparent that an identification code for the individual can simply be provided, to be thereafter telephoned, or otherwise linked, to a central data base terminal to provide all the information there stored—and whether it be as to the identity of a lost child, an injured service man, a terrorist being hunted, an alien attempting to enter a country illegally, a criminal who has escaped, a kidnapped individual, or just about anyone being looked for. As will be seen, depending upon what is to be imparted to the dot, disc or chip implanted in either the human or animal tooth, or on its face, or on a denture in the case of an individual, the benefits to be derived are numerous, with but a simple technique which, at the same time, is cost effective and non-destructive. The ability to gather this kind of information in a quick, efficient manner, will give advantages which will be readily available to those to whom such information is useful.

In performing the method of the invention, it will be apparent that the information medium can either be "passive" or "active" in operation. Where a "passive" microdot, microdisc or microchip is employed, an electronic scanning, for example, can be of any type of wave form to activate such medium to output its encoded information to a wave form receiver—whether large or small—, and by means of an electronic wave form, sound, light, detection of heat and/or cold temperatures. Where the microdot, microdisc or microchip, etc. is of an "active" transmitting nature, it can be provided with an on-off switch capability, so as to be actuated by the scanner to provide its output information——and with power for the device being provided by the tissues of the body (e.g., saliva), or by self-powered batteries [e.g., Lithium] or by the saliva produced gold and/or silver galvanic action operating batteries.

While there have been described what are considered to be preferred embodiments of the present invention, it will be readily appreciated by those skilled in the art that modifications can be made without departing from the scope of the teachings herein. For example, although the invention has been described in the context of the utilization of a microdot, microdisc or microchip, it will equally be seen that the information indicia can be incorporated as part of a magnetic tape, or by any other means of encoded information medium, and of other materials as well. Similarly, although a preferred form of the invention envisions the placement of such information on the "cheek" side of a tooth, it will be appreciated that the information could be placed on the "tongue" side of the tooth, and still operate in accordance with the invention. And, it will be equally clear that the information indicia could be affixed not only to a "real" tooth, or to a denture, but could be imparted in connection with usage in a crown for an individual, depending upon the particular findings in the patient's mouth at the time that the individual is having such information medium installed. In such arrangement, the dentist can be provided with a series of microdots, microdiscs or microchips, to be inserted into the tooth, onto the tooth surface, or into the denture or crown at the time of visit—and appropriate scanners provided to various school or governmental agencies at later dates to be used in detecting the presence of the medium and the information imparted—either directly from the medium or from information maintained in a data bank. In any events, the output of the indicia information can be easily obtained and identifications maintained current for availability throughout any country and world location—either by telephone or satellite linkage. For at least such reasons, therefore, resort should be had to the claims appended hereto for a correct understanding of the breadth of the coverage herein.

We claim:

1. A method enabling user identification of human and animal subjects, comprising the steps of:
   a. first, permanently affixing an indicia of identification information at a location within a tooth of the subject to be identified;
   b. second, user scanning of said identifying indicia from outside the subject's mouth, for non-destructively out-putting the information thereby stored thereon; and
   c. wherein said second step actuates said affixed indicia to enable said identifying information to be obtained on demand by a user externally scanning said indicia; and
   wherein said indicia of identification is in the form of an "active" medium, transmitting its stored information and acted upon by the scanning of said second step, to enable its stored information to be read upon interrogation scanning.

2. The method of claim 1 wherein said first step affixes one of a microdot, microdisc and microchip to said tooth containing the information indicia pertaining to the subject to be identified.

3. The method of claim 1 wherein said first step affixes the information indicia to the face surface of said tooth.

4. The method of claim 1 wherein said first step affixes the information indicia to said tooth to a predetermined depth.

5. The method of claim 4 wherein said first step includes the substeps of:
   a. First, preparing a cavity within said tooth to receive said information indicia at said predetermined depth;
   b. Second, placing said information indicia within said cavity;
   c. Third, layering a clear composite material over said indicia to protect said indicia and to fill the cavity so formed.

6. The method of claim 5 wherein said first sub-step includes the step of using a self-limiting dental drill to prepare said tooth cavity of a size correspondent to receive that of said information indicia.

7. The method of claim 5 wherein said second sub-step includes the step of cleansing said information indicia of contamination prior to the layering thereover of said composite material in said third sub-step.

8. The method of claim 1 wherein said second step includes electronic scanning of said identifying indicia for out-putting the information stored thereon upon demand of a user externally scanning said indicia.

* * * * *